(12) United States Patent
Samproni

(10) Patent No.: US 9,791,400 B2
(45) Date of Patent: Oct. 17, 2017

(54) INTERDIGITATED ARRAY AND METHOD OF MANUFACTURE

(71) Applicant: Siemens Healthcare Diagnostics Inc., Tarrytown, NY (US)

(72) Inventor: Jennifer A. Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 407 days.

(21) Appl. No.: 14/359,792

(22) PCT Filed: Nov. 19, 2012

(86) PCT No.: PCT/US2012/065834
§ 371 (c)(1),
(2) Date: May 21, 2014

(87) PCT Pub. No.: WO2013/078127
PCT Pub. Date: May 30, 2013

(65) Prior Publication Data
US 2014/0367255 A1    Dec. 18, 2014

Related U.S. Application Data

(60) Provisional application No. 61/562,645, filed on Nov. 22, 2011, provisional application No. 61/577,933, filed on Dec. 20, 2011.

(51) Int. Cl.
*G01N 27/327* (2006.01)
*G01N 27/12* (2006.01)
*H05K 3/32* (2006.01)

(52) U.S. Cl.
CPC ......... *G01N 27/327* (2013.01); *G01N 27/127* (2013.01); *H05K 3/321* (2013.01); *Y10T 29/49155* (2015.01)

(58) Field of Classification Search
CPC .................................................. G01N 27/327
See application file for complete search history.

(56) References Cited

U.S. PATENT DOCUMENTS

| | | | | |
|---|---|---|---|---|
| 3,701,317 A | * | 10/1972 | Miyamoto | H01B 1/00 101/163 |
| 6,175,419 B1 | | 1/2001 | Hague et al. | |

(Continued)

FOREIGN PATENT DOCUMENTS

| JP | S6488354 A | 4/1989 |
|---|---|---|
| JP | H06222035 A | 8/1994 |

(Continued)

OTHER PUBLICATIONS

Bard et al., "Digital Simulation of the Measured Electrochemical Response of Reversible Redox Couples at Microelectrode Arrays: Consequences Arising from Closely Spaced Ultramicroelectrodes", Sep. 1986, Analytical Chemistry, vol. 58, No. 11, American Chemical Society: pp. 2321-2331.

(Continued)

*Primary Examiner* — Jill Warden
*Assistant Examiner* — Matthew Krcha
(74) *Attorney, Agent, or Firm* — Kyle D. Petaja

(57) ABSTRACT

An automated feed manufacturing product is disclosed. The automated feed manufacturing product is provided with a flexible substrate having a plurality of card zones with the card zones defining sensing areas with sensor units formed within the sensing areas. The sensor units have a first electrode having first fingers, and a second electrode having second fingers and with the first fingers interleaved with the second fingers and with the first fingers spaced away from the second fingers. The sensor units also comprising biomolecule receptors on the flexible web between the first electrode and the second electrode such that a physical property of the first electrode relative to the second electrode is (Continued)

effected upon one or more of the biomolecule receptors binding to a biomolecule. The automated feed manufacturing product can be formed as a continuous web, or discrete sheets formed using a sheet feeder that picks up and processes the discrete sheets.

9 Claims, 4 Drawing Sheets

(56)  References Cited

U.S. PATENT DOCUMENTS

| | | | |
|---|---|---|---|
| 6,289,729 | B1 | 9/2001 | Haque et al. |
| 6,635,895 | B2 | 10/2003 | Haque et al. |
| 2003/0188427 | A1* | 10/2003 | Say ............... A61B 5/14532 29/846 |
| 2004/0022677 | A1* | 2/2004 | Wohlstadter ........ B01L 3/5085 422/52 |
| 2006/0072944 | A1* | 4/2006 | Sharma ................ H04L 45/00 399/308 |
| 2006/0175431 | A1 | 8/2006 | Renn et al. |
| 2007/0145356 | A1 | 6/2007 | Amlani et al. |
| 2007/0228439 | A1 | 10/2007 | Duan et al. |
| 2007/0256944 | A1 | 11/2007 | Lin et al. |
| 2009/0084686 | A1 | 4/2009 | Yun et al. |
| 2009/0294303 | A1 | 12/2009 | Fischer et al. |
| 2010/0084599 | A1* | 4/2010 | Lewis ................. B22F 1/0022 252/62.2 |
| 2010/0270174 | A1 | 10/2010 | Chen et al. |
| 2011/0017594 | A1 | 1/2011 | Petisce et al. |
| 2011/0269648 | A1 | 11/2011 | Schwartz |

FOREIGN PATENT DOCUMENTS

| | | |
|---|---|---|
| JP | 2002506205 A | 2/2002 |
| JP | 2003529061 A | 9/2003 |
| JP | 2005512027 A | 4/2005 |
| JP | 2005520130 A | 7/2005 |
| JP | 2006504919 A | 2/2006 |
| JP | 2006507692 A | 3/2006 |
| JP | 2009524046 A | 6/2009 |
| JP | 2009524811 A | 7/2009 |
| JP | 2009543090 A | 12/2009 |
| WO | 9945375 A1 | 9/1999 |
| WO | 2007084077 A1 | 7/2007 |
| WO | 2008007822 A1 | 1/2008 |
| WO | 2010056826 A1 | 5/2010 |

OTHER PUBLICATIONS

Van Gerwen et al., "Nanoscaled Interdigitated Electrode Arrays for Biochemical Sensors", Sensors and Actuators B, Mar. 1998, vol. 49, Elsevier Science S.A.: pp. 73-80.
Cohen et al., "Large-area Interdigitated Array Microelectrodes for Electrochemical Sensing", Sensors and Actuators B, 2000, vol. 62, Elsevier Sciences S.A.: pp. 23-29.
Do, Jaephil, A Disposable Polymer Lab-On-A-Chip With Micro/Nano Biosensor for Magnetic Nano Bead-Based Immunoassay, Aug. 14, 2006, Division of Research and Advanced Studies of the University of Cincinnati, pp. 1-122.
Bowen et al., "Optimisation of Interdigitated Electrodes for Piezoelectric Actuators and Active Fibre Composites", J. Electroceram, 2006, vol. 16, Springer: pp. 263-269.
King, Bruce, "Fine-Line, Non-Contact Printing for High Efficiency Solar Cells", Apr. 9, 2009, Optomec, pp. 1-52.
International Search Report and Written Opinion of International Application No. PCT/US2012/065834 dated Feb. 7, 2013.
European Search Report and Written Opinion of European Patent Application No. EP 12851016 mailed on Jul. 8, 2015.

* cited by examiner

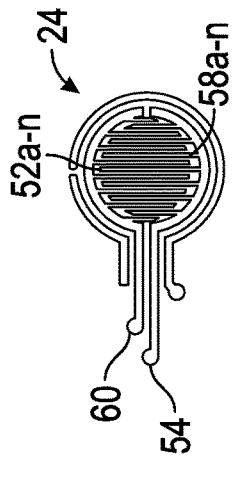
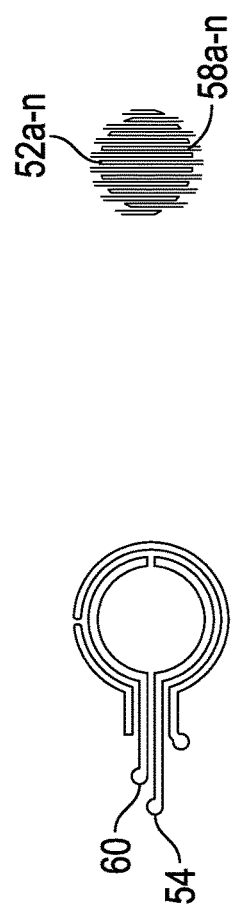
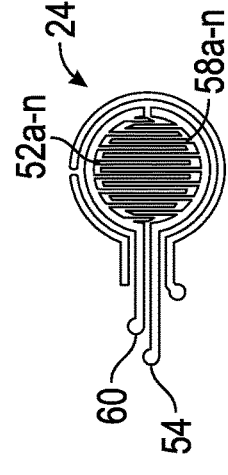
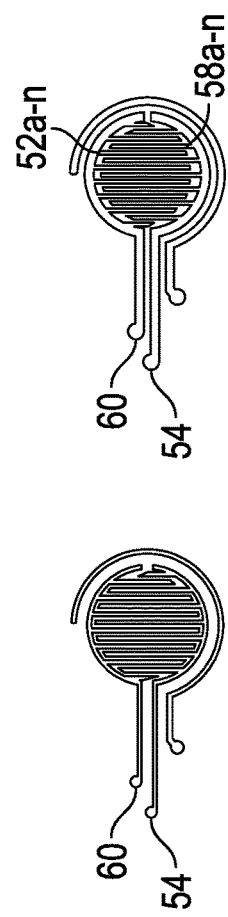

INTERDIGITATED ARRAY AND METHOD OF MANUFACTURE

CROSS-REFERENCE TO RELATED APPLICATIONS

This application claims benefit under 35 U.S.C. 119(e) of U.S. Ser. No. 61/562,645, filed Nov. 22, 2011 and of U.S. Ser. No. 61/577,933 filed Dec. 20, 2011. The entire contents of the above-referenced applications are expressly incorporated herein by reference.

STATEMENT REGARDING FEDERALLY SPONSORED RESEARCH AND DEVELOPMENT

Not Applicable.

BACKGROUND

A sensor (also called detector) is a device that measures a physical quantity and converts it into a signal which can be read by an observer or by an instrument. For example, a mercury-in-glass thermometer converts the measured temperature into expansion and contraction of a liquid which can be read on a calibrated glass tube. A thermocouple converts temperature to an output voltage which can be read by a voltmeter. For accuracy, most sensors are calibrated against known standards.

In biomedicine and biotechnology, sensors which detect analytes having a biological component, such as cells, protein, or nucleic acid are called biosensors. Biosensors can be used for both in vitro and in vivo applications.

Typically, biosensors are exposed to a biological specimen, such as blood or urine and are used to detect predetermined analytes within the biological specimen. The biosensor may then be exposed to a transducer or detector element which may work in a physiochemical manner using a sensing medium such as light, electricity, piezoelectric, electrochemical or the like. In any event, the transducer or detector element transforms a signal from the biosensor into another signal that can be more easily measured and quantified. The signal produced by the transducer or detector element may be provided to a reader device having associated electronics, signal processors and/or a display to provide the results in a user readable format. For example, the results can be provided on a graphical display.

In any event, one type of biosensor that has been used in the past is based upon technology including an interdigitated sensor array which achieves amplification of a sensor signal. The interdigitated sensor array is provided with at least two microelectrodes, both of which have fingers which are spaced apart and interleaved in an interdigitated fashion. Each of the microelectrodes is provided with a relatively large trace connected to a plurality of relatively fine traces. Exemplary interdigitated sensor arrays have been described in a variety of articles, such as *Large-area interdigitated array microelectrodes for electrochemical sensing*, Sensors and Actuators, Adam E. Cohen, and Roderick R. Kunz (2000) pgs. 23-29; *Digital Simulation of the Measured Electrochemical Response of Reversible Redox Couples at Microelectrode Arrays: Consequences Arising from Closely Spaced Ultramicroelectrodes*, Allen J. Bard et al., Anal. Chem. 1986, 58, 2321-2331; and United States Patent Application Number 2009/0084686, filed on Feb. 27, 2008; and United States Patent Application Number 2007/0145356, filed on Dec. 25, 2005.

Limitations in the trace dimensions (the width of the interdigitated fingers) and space dimensions (the edge-to-edge distance of the interdigitated fingers) are encountered using standard screen printing, electrodeposition and laser ablation approaches to manufacturing the interdigitated sensor arrays. For these reasons, in the past, the interdigitated sensor arrays have been fabricated using semi-conductor type fabrication techniques including photolithography using substrates suitable for use in semiconductor fabrication. Exemplary prior art substrates include silicon dioxide, glass, ceramic, a semiconductor material, or a flexible material. See for example, paragraph [0023] of United States Patent Application Number 2007/0145356.

However, to Applicant's knowledge, there has not been a cost-effective method for fabricating a biosensor with an interdigitated sensor array that makes such biosensor available to be mass produced and widely used as a disposable sensor for testing biological specimens, such as blood and urine. It is to such a method and apparatus for cost-effectively producing biosensors that the present disclosure is directed.

BRIEF DESCRIPTION OF THE DRAWINGS

The accompanying drawings, which are incorporated in and constitute a part of this specification, illustrate one or more implementations described herein and, together with the description, explain these implementations. In the drawings:

FIGS. 4a, 4b and 4c cooperate to illustrate an exemplary method for making a sensor unit in accordance with the present disclosure.

FIGS. 5a, 5b, and 5c cooperate to illustrate another exemplary method for making a sensor unit in accordance with the present disclosure.

DETAILED DESCRIPTION

The following detailed description refers to the accompanying drawings. The same reference numbers in different drawings may identify the same or similar elements.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

Finally, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Circuitry, as used herein, could be analog and/or digital, components, or one or more suitably programmed microprocessors and associated hardware and software, or hardwired logic. Also, "components" may perform one or more functions. The term "component," may include hardware, such as a processor, an application specific integrated circuit (ASIC), or a field programmable gate array (FPGA), or a combination of hardware and software. Software includes one or more computer executable instructions that when executed by one or more component cause the component to perform a specified function. It should be understood that the algorithms described herein are stored on one or more non-transient memory. Exemplary non-transient memory includes random access memory, read only memory, flash memory or the like. Such non-transient memory can be electrically based or optically based.

Figure 1:
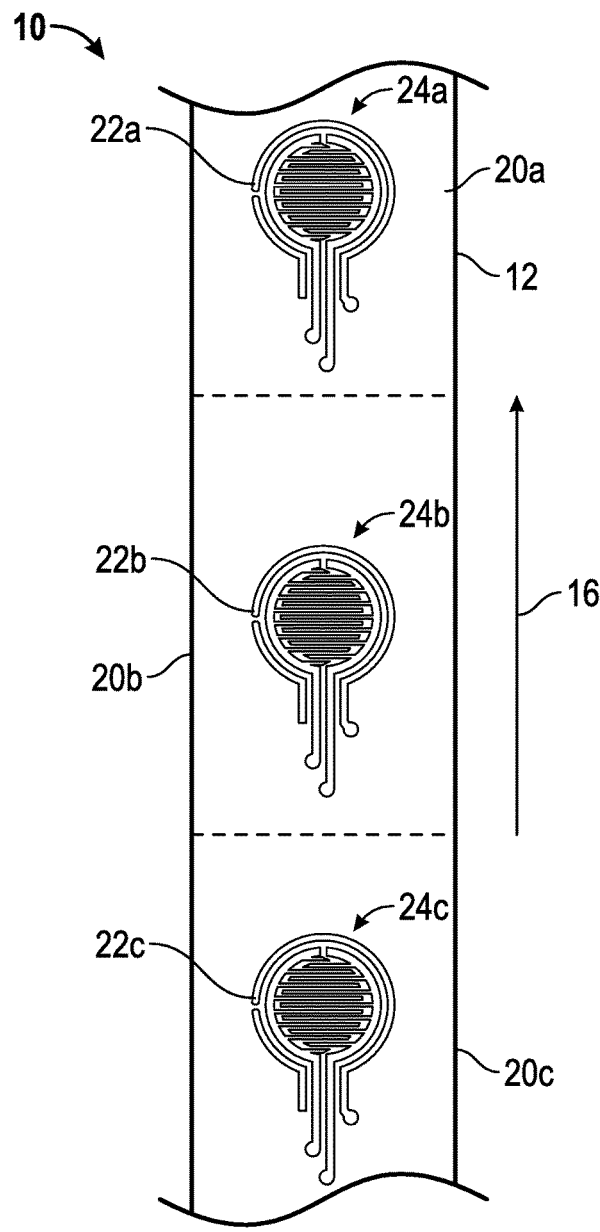
FIG. 1 is a partial, top plan view of a web product having a plurality of card zones defining sensing areas with sensor units formed within the sensing areas in accordance with the present disclosure.

Referring now to the Figures and in particular to FIG. 1, shown therein is an exemplary automated feed manufacturing product 10 constructed in accordance with the present disclosure. The automated feed manufacturing product 10 can be formed as a continuous web, or discrete sheets formed using one or more sheet feeder that picks up and processes the discrete sheets as described below. As an example, the automated feed manufacturing product 10 will described as a web product formed from at least one flexible web 12. In general, the at least one flexible web 12 is a continuous sheet of transparent, translucent or opaque material moving in a direction of travel 16, which is generally along the longitudinal axis of the flexible web 12. The flexible web 12 is guided by suitable web guiding equipment including rollers, sensors and a web guide controller. Web guiding equipment is known in the art, and a detailed description of how to make and use same is not deemed necessary herein to teach one skilled in the art how to make and use the automated feed manufacturing product 10. For example, suitable web guiding equipment is described in U.S. Pat. Nos. 6,635,895, 6,289,729, or 6,175,419, the entire contents of which are hereby incorporated by reference.

Figure 6:
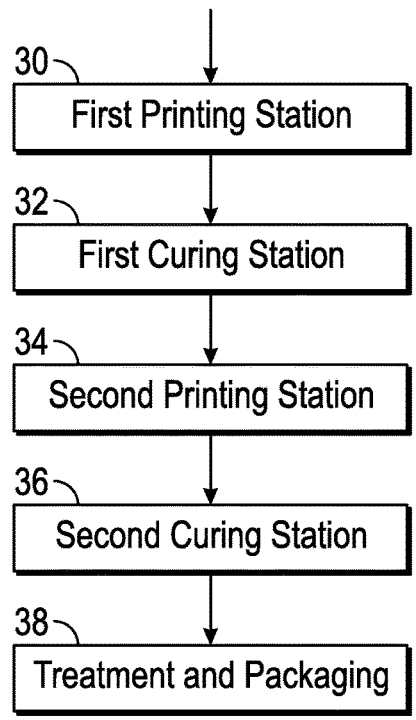
FIG. 6 is a flow diagram illustrating an exemplary method for making the web product in accordance with the present disclosure.

The flexible web 12 has a plurality of card zones 20 which are designated in FIG. 1 with the reference numerals 20a, 20b and 20c. The card zones 20a, 20b and 20c define sensing areas 22a, 22b and 22c. Sensor units 24a, 24b and 24c are formed within the sensing areas 22a, 22b and 22c as the flexible web 12 is passed though various equipment. For example, as shown in FIG. 6, the flexible web 12 can be passed through a first printing station 30, a first curing station 32, a second printing station 34, a second curing station 36, and treatment and packaging equipment 38. The treatment and packaging equipment 38 applies biomolecule receptors (not shown) to the sensor units 24a, 24b and 24c for sensing various types of analytes, and may also include cutting equipment for forming sensor cards 44 from the flexible web 12. The biomolecule receptors can be sensor immobilized or non-sensor immobilized.

Figure 2:
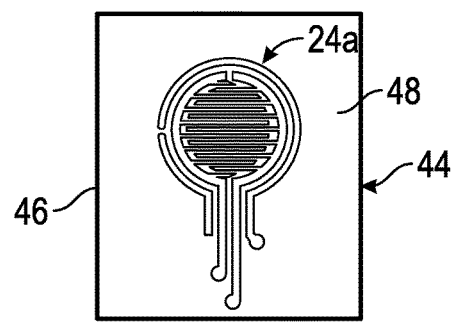
FIG. 2 is a top plan view of an exemplary sensor card constructed in accordance with the present disclosure.

An exemplary sensor card 44 is shown in FIG. 2. The sensor card 44 includes a substrate 46 which may have been a part of the flexible web 12. The substrate 46 has a first surface 48 upon which one or more of the sensor units 24a, 24b and 24c are formed. The substrate 46 can be constructed of a material that is capable of being guided, yet can also be exposed to a biological specimen such as a cheek swab, blood, plasma, urine or the like without shrinkage. For example, the substrate 46 can be selected from a group consisting of paper, and plastics, including polyimide, polyethylene, polyethylene terephthalate, polyester, and combinations thereof.

Figure 3:
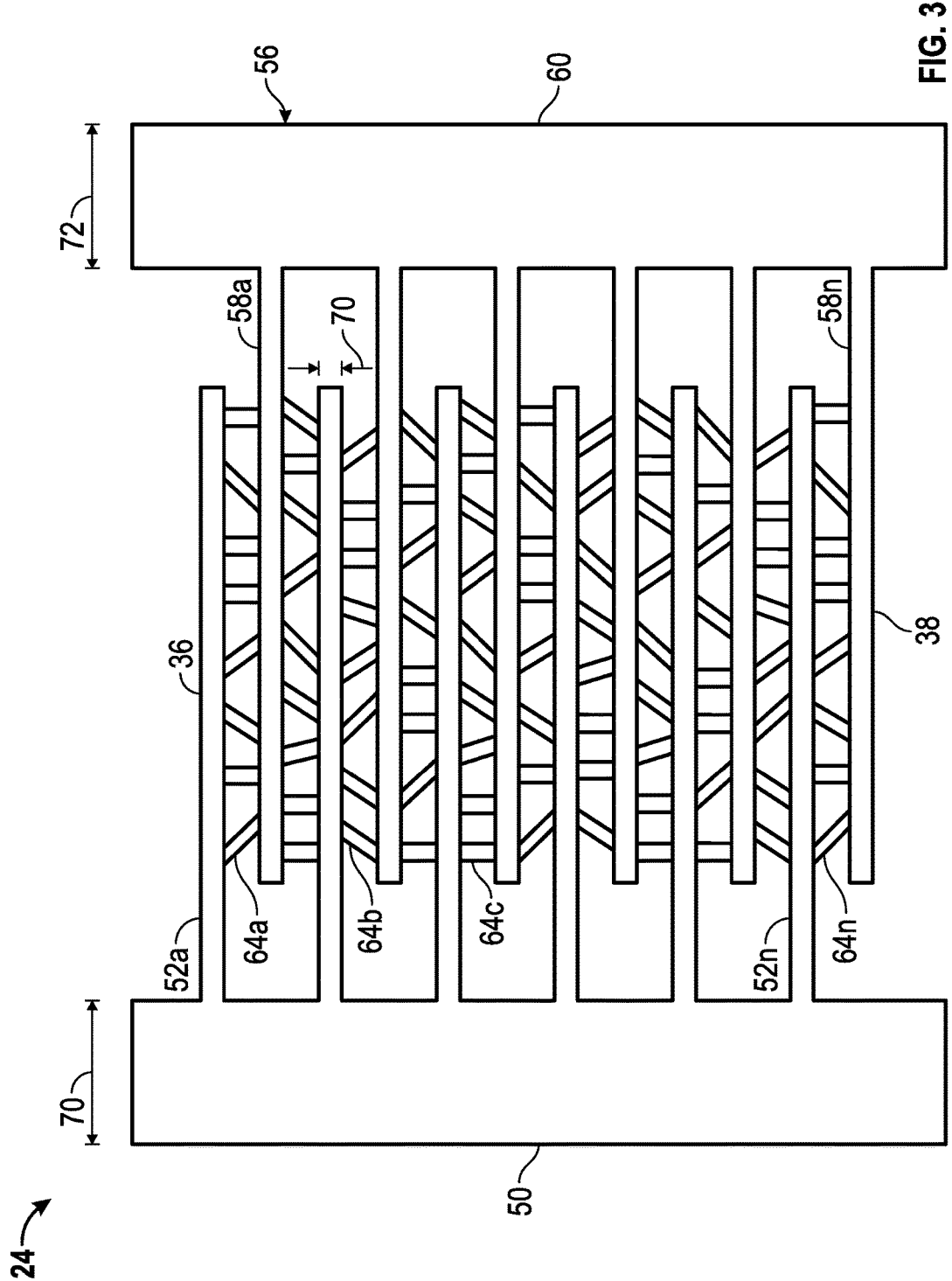
FIG. 3 is a top plan view of an exemplary sensor unit constructed in accordance with the present disclosure.

Referring now to FIG. 3, the one or more sensor unit 24 has a first electrode 50 having first fingers 52a-n, and a first conducting element 54; and a second electrode 56 having second fingers 58a-n and a second conducting element 60. The first fingers 52a-n are interleaved with the second fingers 58a-n and the first fingers 52a-n are spaced away from the second fingers 58a-n. The first fingers 52a-n, the first conducting element 54, the second fingers 58a-n, and the second conducting element 60 are constructed of one or more electrically conductive material, such as one or more layers of cured conductive ink.

In general, conductive ink includes a carrier (e.g., a liquid solvent that evaporates after deposition) and particles of one or more conductive material, or other functional material that remain on the substrate 46. Any type of conductive material can be utilized so long as a particle size of the conductive material is suitable for the printing technology being used to apply the conductive material to the flexible web 12. For example, the conductive material can be selected from a group consisting of nanoparticle aluminum, nanoparticle gold, nanoparticle silver, nanoparticle copper, carbon nanotubes, nanoparticle graphene, and nanoparticle platinum. The conductive ink can be cured using any suitable curing process at the first and second curing stations 32 and 36, such as heat, pulsed light curing and/or laser sintering.

The one or more sensor unit 24 also comprise biomolecule receptors 64a-n on the substrate 46 between the first fingers 52a-n and the second fingers 58a-n such that a physical property of the first fingers 52a-n relative to the second fingers 58a-n is effected upon one or more of the biomolecule receptors 64a-n binding to a biomolecule. The physical property of the first fingers 52a-n relative to the second fingers 58a-n refers to conductivity, resistance, and/or capacitance. Thus, one or more biomolecules binding to the biomolecule receptors 64a-n effects the conductivity, resistance and/or capacitance measured across the first electrode 50 and the second electrode 56.

The first fingers 52a-n are spaced a distance away from the second fingers 58a-n to permit binding of biomolecules to the biomolecule receptors 64a-n to establish an electrical connection between the first fingers 52a-n and the second fingers 58a-n. The edge to edge spacing between the first fingers 52a-n and the second fingers 58a-n is referred to herein as a space and can be between 10 nanometers and 1 millimeter. For example, a suitable space may be between 20 microns and 0.2 microns. For the purposes of interdigitated arrays (IDAs), the space is an important feature in signal amplification. Aspect ratio (also known as z-height) is also a significant influence in signal amplification. The trace, or line width, plays a lesser role in signal amplification. In addition, in an exemplary embodiment, the first fingers 52*a-n* and the second fingers 58*a-n* have a thickness between 0.01 micrometers and 100 micrometers. As will be discussed in more detail below, in one embodiment, a edge-to-edge space of less than 10 microns can be achieved using an aerosol jetting apparatus to form the first fingers 52*a-n* and the second fingers 58*a-n*. An exemplary aerosol jetting apparatus which could be used in this application is manufactured by Optomec, Inc. For example, an exemplary aerosol jetting apparatus is described in U.S. Patent publication no. 2006/0175431.

The aerosol jetting apparatus preferably functions without directly contacting the substrate 46, and may be operated at room temperature.

Referring now to FIGS. 4*a*, 4*b* and 4*c*, shown therein is an exemplary method for making the sensor unit 24 in accordance with the present disclosure. In general, methods disclosed herein for making the sensor unit 24 utilize a hybrid manufacturing approach using two different types of printing technologies. As will be discussed in more detail below, the parts of the first and second electrodes 50 and 56 have different geometries including widths and pitches.

As shown in FIG. 4*a*, parts of the first and second electrodes 50 and 56 having a relatively larger width and/or pitch (which may be referred to herein as "relatively larger portions") can be formed using conductive ink applied to the flexible web 12 using one or more first printing technology. The first printing technology can be a non-aerosol jetting technology using a non-aerosol jetting apparatus selected from a group consisting of a screen printing apparatus, a stenciling apparatus, an electro-deposition apparatus, a sputtering apparatus, a laser ablation apparatus and combinations thereof. Exemplary parts of the first and second electrodes 50 and 56 that can be formed using one or more first printing technology include the first conducting element 54 and the second conducting element 60. The sensor unit 24 shown in FIG. 3 is a two-electrode design where the first conducting element 54 is a counter electrode, and the second conducting element 60 is a working electrode. The sensor unit 24*a* shown in FIG. 2 has a four electrode design (e.g. the working electrode is interdigitated, thus comprising two electrodes, the counter electrode and the reference electrode). For the interdigitated design, a reference electrode may be omitted if that configuration is compatible with the sensor usage. In addition, the sensor unit may also be constructed as a three electrode design having a counter electrode, a working electrode and a reference electrode.

As shown in FIG. 4*b*, parts of the first and second electrodes 50 and 56 having a finer width or pitch (which may be referred to herein as "relatively finer portions") can be formed using conductive ink having a particle size less than or equal to 5 microns and applied to the flexible web 12 using a second printing technology such as aerosol jetting. Exemplary parts of the first and second electrodes 50 and 56 that can be formed using the second printing technology include the first and second fingers 52*a-n* and 58*a-n*. However, it should be understood that other parts of the first and second electrodes 50 and 56 can be formed with the second printing technology, such as the first conducting element 54 and the second conducting element 60.

As shown in FIG. 4*c*, the sensor unit 24 can be a composite formed by the combination of additive manufacturing processes including the first and second printing technologies discussed above. In other words, to make the sensor unit 24, a first conductive ink is applied to the flexible web 12 and/or substrate 46 in a first pattern to form the first conducting element 54 and the second conducting element 60. The first and second conducting elements 54 and 60 have first and second widths 70 and 72 as shown in FIG. 3.

A second conductive ink is applied to the flexible web 12 and/or substrate 46 with an aerosol jetting apparatus in a second pattern to form first fingers 52*a-n* interleaved with the second fingers 58*a-n*. The first and second fingers 52*a-n* and 58*a-n* have third and fourth widths 74 and 76 that are less than the first and second widths 70 and 72 of the first and second conducting elements 54 and 60.

The widths 70 and 72 can vary. Currently, the widths 70 and 72, as well as the pitch between the first fingers 52*a-n* and the second fingers 58*a-n* can be in a range between 1 micron and 20 microns with the current aerosol jetting capability. However, sub-micron spacing would offer an improvement as the aerosol jetting technology improves. In addition, the first fingers 52*a-n* and the second fingers 58*a-n* have a thickness which also offers amplification and can be achieved using the aerosol jetting technology by altering % conductive metal in the conductive ink or by multiple jet passes. The thickness of the first fingers 52*a-n* and the second fingers 58*a-n* can be in a range from 20 nanometers to 750 nanometers, and is more preferably in a range between 200 nanometers and 500 nanometers.

The first and second patterns overlap such that the first conducting element 54 and the first fingers 52*a-n* are electrically connected to form the first electrode 50 of the sensor unit 24, and the second conducting element 60 are electrically connected to the second fingers 58*a-n* to form the second electrode 56 of the sensor unit 24.

The first and second conductive inks can be the same or different. For example, the first conductive ink can have a particle size greater than 5 microns, while the second conductive ink can have a particle size less than or equal to 5 microns. Further, the types of conductive materials in the first and second conductive inks can be the same or different. Alternatively, the first and second conductive inks can both have a particle size less than or equal to 5 microns.

In any event, once the first conductive ink is applied, the flexible web 12 and/or the substrate 46 can be passed through the first curing station 32, and after the second conductive ink is applied, the flexible web 12 and/or the substrate 46 can be passed through the second curing station 36.

The first and second electrodes 50 and 52 can be formed with a single layer, or multiple layers utilizing the same or different types of conductive ink. For example, the second conductive ink can be applied to the flexible web 12 and/or the substrate 46 to form a first layer of the predetermined pattern having the first fingers 52*a-n* of the first electrode 50 interleaved with second fingers 58*a-n* of the second electrode 56, followed by the application of a third conductive ink forming a second layer of the predetermined pattern covering the first layer of the predetermined pattern.

Once the first and second electrodes 50 and 56 are formed, then the biomolecule receptors 64*a-n* can then be applied, and the flexible web 12 can be cut to form the sensors cards 44.

Shown in FIGS. 5*a*, 5*b*, and 5*c* is another exemplary method for making the sensor unit 24 in accordance with the present disclosure. In particular, as shown in FIG. 5*a*, the aerosol jetting apparatus can be used to form the first and second conducting elements 54 and 60; and the first and second fingers 52*a-n* and 58*a-n* of the first and second electrodes 50 and 56. For example, the first and second conducting elements 54 and 60; and the first and second fingers 52*a-n* and 58*a-n* can be formed using nanoparticle silver and having a width of 0.0004 inches. As shown in FIG.

5b, the aerosol jetting apparatus is then used to apply a second layer of conductive ink to the first and second conducting elements 54 and 60; and the first and second fingers 52a-n and 58a-n using a different material, such as graphite, and a different width of 0.0012 inches. Any remaining portion(s) of the sensor unit 24 can then be formed with the first printing technology as shown in FIG. 5c.

Figure 7:
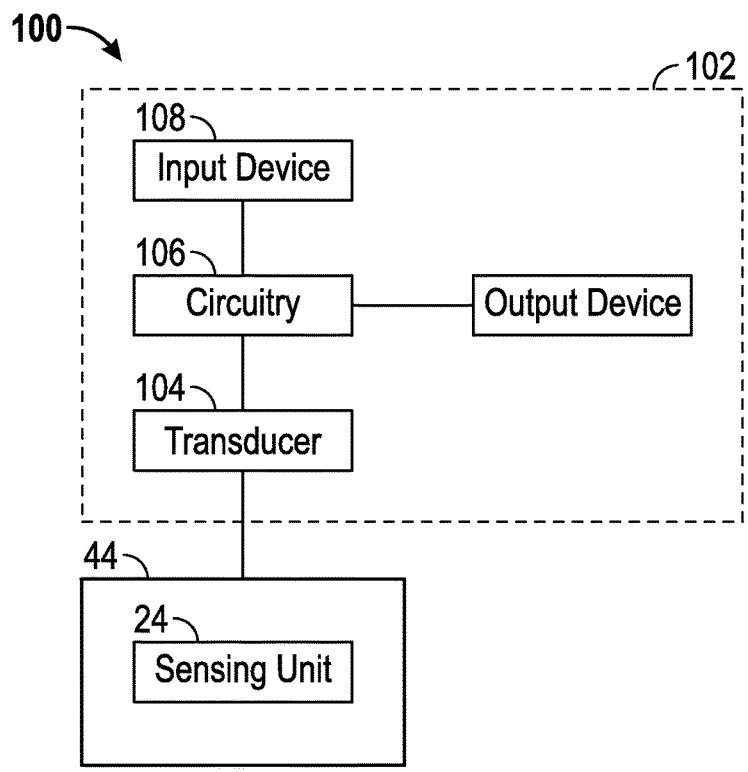
FIG. 7 is a block diagram of a biosensor kit constructed in accordance with the present disclosure.

Shown in FIG. 7 is an exemplary biosensor kit 100 constructed in accordance with the present disclosure. In general, the biosensor kit 100 includes one or more of the sensor card 44, and a reader device 102. The reader device 102 is provided with a transducer 104 operable to read the one or more sensor unit 24 on the substrate 46 of the sensor card 44, and circuitry 106 to provide results of the reading of the one or more sensor unit 24 in a user-perceivable format. The reader device 102 can also be provided with one or more input device 108 to permit user and/or machine input into the reader device 102, and one or more output device 110. Exemplary input devices 108 include a network port, a keyboard, a touchscreen or the like. Exemplary output devices 110 include a display, printer, network port or the like.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure. For example, the order of applying the relatively larger portions of the sensor unit 24 with the non-aerosol jetting technology can be prior to application of the relatively finer portions of the sensor unit 24 with the aerosol jetting technology, or vice-versa. Further, although the sensor card 44 is described herein as being formed from the flexible web 12, it should be understood that the sensor card 44 could be formed in other manners, such as using a continuous process with discrete sheets and a sheet feeder rather than a continuous role of plastic or paper substrate material.

Also, certain portions of the implementations may have been described as "components" or circuitry 106 that perform one or more functions. The term "component" or "circuitry" may include hardware, such as a processor, an application specific integrated circuit (ASIC), or a field programmable gate array (FPGA), or a combination of hardware and software.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

What is claimed is:

1. A method of making a sensor card, comprising the steps of:

applying a first conductive ink to a substrate in a first pattern to form a first conducting element and a second conducting element, the first and second conducting elements having first and second widths, the first conductive ink having a particle size of greater than 5 microns;

applying a second conductive ink to the substrate with an aerosol jetting apparatus in a second pattern to form first fingers interleaved with second fingers, the first and second fingers having third and fourth widths that are less than the first and second widths of the first and second conducting element, the first fingers being spaced a distance from the second fingers between 10 nanometers and 1 millimeter, the second conductive ink having a particle size of less than or equal to 5 microns, wherein the first conducting element and the first fingers are electrically connected to form a first electrode of a sensor unit, and the second conducting element are electrically connected to the second fingers to form a second electrode of the sensor unit; and wherein the step of applying the first conductive ink to the substrate is defined further as applying the first conductive ink to the substrate utilizing a non-aerosol jetting apparatus selected from a group consisting of a screen printing apparatus, a stenciling apparatus, an electro-deposition apparatus, a sputtering apparatus, a jetting apparatus, a laser ablation apparatus and combinations thereof; and further comprising the step of applying sensor-immobilized biomolecule receptors on the substrate between the first electrode and the second electrode such that the first electrode is electrically connected to the second electrode upon one or more of the biomolecule receptors binding to a biomolecule.

2. The method of claim 1, further comprising a step of passing the substrate through a first curing station after the first conductive ink is applied to the substrate.

3. The method of claim 1, further comprising a step of passing the substrate through a second curing station after the second conductive ink is applied to the substrate.

4. The method of claim 1, wherein the substrate is a flexible web guided by a web guiding system.

5. The method of claim 4, wherein the flexible web is constructed of a material selected from a group consisting of paper, a polyamide, a plastic, and combinations thereof.

6. The method of claim 1, wherein the first conductive ink is different from the second conductive ink.

7. The method of claim 1, wherein the step of applying the second conductive ink to the substrate is defined further as applying the second conductive ink to the substrate to form a first layer of the predetermined pattern having the first fingers of the first electrode interleaved with second fingers of the second electrode, and wherein the method further comprises the step of applying a third conductive ink to the substrate forming a second layer of the predetermined pattern covering the first layer of the predetermined pattern having the first fingers of the first electrode interleaved with second fingers of the second electrode.

8. The method of claim 7, wherein the second conductive ink is different from the third conductive ink.

9. The method of claim 7, wherein the second conductive ink is the same as the third conductive ink.

* * * * *